(12) United States Patent
Peyman

(10) Patent No.: US 8,517,944 B2
(45) Date of Patent: Aug. 27, 2013

(54) METHOD AND SYSTEM FOR THREE-DIMENSIONAL (3D) IMAGING OF BIOLOGICAL STRUCTURES

(76) Inventor: Gholam Peyman, Sun City, AZ (US)

(*) Notice: Subject to any disclaimer, the term of this patent is extended or adjusted under 35 U.S.C. 154(b) by 7 days.

(21) Appl. No.: 13/066,012

(22) Filed: Apr. 4, 2011

(65) Prior Publication Data
US 2012/0089021 A1   Apr. 12, 2012

Related U.S. Application Data

(60) Provisional application No. 61/343,890, filed on May 5, 2010.

(51) Int. Cl.
*A61B 8/00* (2006.01)
(52) U.S. Cl.
USPC .......................................................... 600/439
(58) Field of Classification Search
USPC .......................................................... 600/439
See application file for complete search history.

(56) References Cited

U.S. PATENT DOCUMENTS

| | | | | |
|---|---|---|---|---|
| 4,576,176 A | * | 3/1986 | Myers | 600/459 |
| 5,056,522 A | * | 10/1991 | Matsumura et al. | 600/405 |
| 5,369,454 A | | 11/1994 | Reinstein et al. | |
| 5,377,685 A | * | 1/1995 | Kazi et al. | 600/463 |
| 7,618,372 B2 | * | 11/2009 | dela Houssaye | 600/452 |
| 8,249,695 B2 | * | 8/2012 | Grenon et al. | 600/476 |
| 2002/0169491 A1 | * | 11/2002 | Foster et al. | 607/122 |
| 2003/0004416 A1 | * | 1/2003 | Phillips et al. | 600/459 |
| 2003/0229331 A1 | * | 12/2003 | Brisken et al. | 604/500 |
| 2005/0143664 A1 | * | 6/2005 | Chen et al. | 600/478 |
| 2006/0058664 A1 | * | 3/2006 | Barthe et al. | 600/439 |
| 2007/0239000 A1 | * | 10/2007 | Emery et al. | 600/437 |
| 2009/0105597 A1 | * | 4/2009 | Abraham | 600/466 |

OTHER PUBLICATIONS

T. Boker, M. Spitznas, "Ultrasound Biomicroscopy for Examination of the Sclerotomy Site After Pars Plana Vitrectomy", American Journal of Ophthalmology, vol. 118, No. 6, pp. 813-815 (1994).
C. Azzolini, L. Pierro, M. Condenotti, F. Bandello, R. Brancato, "Ultrasound Biomicroscopy Following the Intraocular Use of Silicone Oil", International Ophthalmology, vol. 19(3), pp. 191-195 (1995).
L. Zografos, L. Chamot, L. Bercher, A. Schalenbourg, E. Egger, C. Gailloud, "Contribution of Ultrasound Biomicroscopy to Conservative Treatment of Anterior Uveal Melanoma", Klinische Monatsblatter fur Augenheilkunde, vol. 208(5), pp. 414-417 (1996).
A. Minamoto, K. E. Nakano, S. Tanimoto, Y. Takeda, "Ultrasound Biomicroscopy in the Diagnosis of Persistent Hypotony After Vitrectomy", American Journal of Ophthalmology, vol. 123(5), pp. 711-713 (1997).

* cited by examiner

*Primary Examiner* — Jonathan Cwern
(74) *Attorney, Agent, or Firm* — The Law Office of Patrick F. O'Reilly, III, LLC

(57) ABSTRACT

An ultrasonic scanning apparatus that includes a unique ultrasonic array to transmit ultrasonic energy to a biological structure, such as an eye. The ultrasonic array provides specific three-dimensional (3-D) information relating to the eye and precise volumetric information relating to structures associated therewith, such as a tumor, prior, during and/or after treatment. The ultrasonic array can also be combined with a therapeutic ultrasonic unit for real-time 3-D observation of a structure and the focal point of the transmitted therapeutic beam(s) on a monitor during the treatment of a structure, e.g., treatment of a lesion.

15 Claims, 5 Drawing Sheets

METHOD AND SYSTEM FOR THREE-DIMENSIONAL (3D) IMAGING OF BIOLOGICAL STRUCTURES

CROSS-REFERENCE TO RELATED APPLICATIONS

This application claims the benefit of U.S. Provisional Application No. 61/343,890, filed May 5, 2010.

FIELD OF THE INVENTION

The present invention relates generally to methods and systems for imaging bodily structures. More particularly, the present invention relates to apparatus, systems and methods for three-dimensional ultrasonic imaging (i.e. ultrasonography) of biological structures; particularly, structures of an eye.

BACKGROUND OF THE INVENTION

A-scan ultrasound has been used in ophthalmology to analyze eye tissue and/or structures for over half a century. As is well known in the art, an A-scan ultrasound device merely provides one-dimensional information relating to the scanned structure, e.g., length of an eye. Thus, its application was and remains limited.

To overcome the drawbacks associated with A-scan devices, B-scan devices were developed. As is well known in the art, a typical B-scan device provides two-dimensional (2D) information relating to the scanned structure. A B-scan device can thus provide a sectional image of the retina and other eye structures, and facilitate assessments of vitro-retinal relationships more precisely.

As is also well known in the art, earlier B-scan devices typically employed an ultrasonic frequency in the range of 8-10 MHz. Although the resolution of 10 MHz B-scan devices is sufficient to explore the retina as a whole, it does not provide sufficient resolution of anterior segments or regions.

Furthermore, in order to perform an examination of an anterior segment at 10 MHz, it is necessary to implement immersion with appropriate cupules so as to bring the focal zone which is situated at 23 mm onto the anterior segment.

More recently, B-scan devices employing an ultrasonic frequency of 50 MHz were developed. A commercial version of a high frequency B-scan device is the Ultrasound BioMicroscope (UBM) device distributed by Humphrey-Zeiss. A further device is disclosed in U.S. Pat. No. 5,369,454.

Use of the high frequency UBM device facilitated exacting analyses of anterior segments and adjacent areas of the eye. For example, in 1994, Boker, et al. published a study of the sclerotomy site after pars plana vitrectomy (T. Boker, M. Spitznas, *Ultrasound Biomicroscopy for Examination of the Sclerotomy Site After Pars Plana Vitrectomy*, American Journal of Ophthalmology, vol. 15, pp. 813-815 (1994). In 1995, Azzolini, et al. reported imaging the presence of intra-vitreous silicone residue in the anterior portion of the vitreous cavity (C. Azzolini, L. Pierro, M. Condenotti, F. Bandello, R. Brancato, *Ultrasound Biomicroscopy Following the Intraocular Use Of Silicone Oil*, International Ophthalmology, vol. 19(3), pp. 191-195 (1995).

In 1996, Zografos, et al. published a UBM study of 55 cases of uvea melanomas situated in contact with or close to the ciliary body (L. Zografos, L. Chamot, L. Bercher, *Contribution of Ultrasound Biomicroscopy to Conservative Treatment of Anterior Uveal Melanoma*, Klin. Monast. Augen, vol. 208(5), pp. 414-417 (1996). The conclusion of that work did, however, show that the high attenuation of the high frequency ultrasound signal limits the use of a UBM to structures situated in the direct vicinity of the wall of the eye. Nevertheless, the contribution of high frequency signals in monitoring uvea melanomas after conservative treatment was seen to be considerable.

Further, in 1997, Minamoto, et al. employed a high frequency UBM device to study the separation of the ciliary body situated at the junction between the anterior segment and the posterior segment in the event of hypotony after vitrectomy (A. Minamoto, K. E. Nakano, S. Tanimoto, *Ultrasound Biomicroscopy in the Diagnosis of Persistent Hypotony After Vitrectomy*, American Journal of Ophthalmology, vol. 123(5), pp. 711-713 (1997).

There are, however, several drawbacks and disadvantages associated with high frequency B-scan devices. A major drawback associated with high frequency B-scan devices is that they are typically limited to two-dimensional imaging of scanned structures. As is well known in the art, two-dimensional images are not very precise.

A further major disadvantage associated with high frequency B-scan devices is that little, if any, information can be obtained at the focal point of the transmitted therapeutic beam. Thus, the location of a focused beam and its thermal effect on the target structure or tissue cannot be observed in real-time. Real-time information on the status of the tissue response or the thermal effect, such as coagulation or tissue contraction of the deep structures, therefore cannot be obtained.

Further, peripheral lesions are difficult to image and diagnose. Moreover, even if a lesion, e.g. a tumor, is diagnosed, its dimensions must be calculated indirectly and separately.

Volumetric information relating to scanned structures also cannot be obtained with high frequency B-scan devices. Since volumetric information is not possible, imaging of the treated area and actual treatment must be done sequentially.

In view of the aforementioned drawbacks associated with B-scan devices, there have been efforts to develop improved B-scan devices and methods that provide three-dimensional images of scanned structures. Illustrative is the high frequency B-scan device and method disclosed in U.S. Pat. No. 5,369,454.

The device disclosed in U.S. Pat. No. 5,369,454 includes an ultrasound transducer that is mounted on a pair of linear positioners that are at right angles to each other. The use of two linear positioners allows data to be obtained in sequential, parallel scan planes from which three dimensional images are constructed.

Prior to subjecting a patient's eye to an ultrasound scan, a light source is positioned above a liquid bath in which the patient's eye is submerged. A beam of alignment light is directed at the submerged eye and another light source is positioned above the patient's second eye. The second light source is then moved until the patient indicates a fusion of the light sources into a single spot, at which point it is known that the visual axes of the eyes are vertical and aligned.

During scanning, radio frequency echo data are digitized at a high rate (i.e. well above the Nyquist rate) and images are constructed from the stored radio frequency data.

There are several drawbacks and disadvantages associated with the noted B-scan device. A major drawback is that the eye is scanned with a single beam via linear translation of the transducer. The curved specular surfaces of the eye, especially the cornea, thus result in significant signal loss as the angle of the surface departs from the normal to the transducer axis. For this reason, data acquired by linear scanning are typically limited to an area of 3-3.5 mm in diameter of cornea and images of the anterior segment to one quadrant at a time.

Further, during scanning with the B-scan device, as well as most known conventional B-scan devices, the eye is open and the cornea and conjunctiva are exposed to methycellulose and the moving ultrasonic transducer or probe. B-scan devices thus cannot guarantee a sterile field.

The noted B-scan device, and devices similar thereto, have thus not been found useful for clinical routine three dimensional images and/or representations of ocular structures.

It would thus be desirable to provide apparatus, systems and methods for providing rapid, accurate representations of biological structures; particularly eye structures.

It is therefore an object of the present invention to provide apparatus, systems and methods for providing rapid, accurate representations of biological structures; particularly eye structures.

It is another object of the present invention to provide ultrasonic scanning apparatus, systems and methods for providing rapid and accurate three-dimensional (3-D) images of scanned biological structures and/or tissue associated therewith.

It is another object of the present invention to provide ultrasonic scanning apparatus, systems and methods for providing rapid and accurate three-dimensional (3-D) images of scanned biological structures during therapeutic procedures.

It is another object of the present invention to provide ultrasonic scanning apparatus, systems and methods for providing rapid and accurate three-dimensional (3-D) images of scanned biological structures and the focal point of the transmitted therapeutic energy (i.e. beam) during therapeutic procedures.

SUMMARY OF THE INVENTION

The present invention is directed to ultrasonic scanning apparatus, systems and methods that employ a unique ultrasonic array to transmit ultrasonic energy to a biological structure, such as an eye. The ultrasonic array provides specific three-dimensional (3-D) information relating to a biological structure, such as an eye, and precise volumetric information relating to structures associated therewith, such as a tumor, prior, during and/or after treatment. The ultrasonic array can also be combined with a therapeutic ultrasonic unit for real-time 3-D observation of a structure on a monitor during the treatment, e.g., treatment of a lesion as a single procedure.

In one embodiment of the invention, the scanning apparatus and system includes (i) an imaging probe that is adapted to generate and transmit first and second arrays of ultrasonic energy to a biological structure, the first array having a first energy path and a first focal point, the second array having a second energy path and a second focal point, (ii) means for controlling at least one of the first and second energy paths, whereby the first focal point is disposed proximate the second focal point and, whereby stereoscopic visualization of the biological structure is provided, (iii) a therapeutic probe that is adapted to generate and transmit therapeutic energy to the biological structure, the therapeutic energy having a third energy path and a third focal point, (iv) means for simultaneous liner translation of the imaging and therapeutic probe proximate the biological structure, (v) control means for controlling the first and second arrays, therapeutic probe, energy path control means, third energy path, and linear translation control means, and (vi) a processor that is programmed and adapted to receive scanning data from the imaging probe and generate three-dimensional images of the biological structure therefrom.

In some embodiments of the invention, the imaging probe includes first and second energy transducers, the first transducer being adapted to transmit the first array of ultrasonic energy, the second transducer being adapted to transmit the second array of ultrasonic energy.

In some embodiments of the invention, the control means is further adapted to control the ultrasonic energy transmitted by the imaging and therapeutic probes.

In some embodiments of the invention, the ultrasonic energy transmitted by the imaging probe has a frequency in the range of approximately 1-100 MHz.

In some embodiments of the invention, the therapeutic probe comprises a therapeutic ultrasound probe.

In some embodiments of the invention, the therapeutic probe comprises a therapeutic laser probe.

In some embodiments of the invention, the processor is further adapted and programmed to filter extraneous signals to enhance the accuracy of the generated 3-D images.

In some embodiments of the invention, the apparatus includes a video camera.

In some embodiments of the invention, the apparatus further includes a tracking system that is adapted to track movements of the target biological structure.

A key advantage of the invention is the provision of ultrasonic scanning apparatus, systems and methods that provide rapid and accurate three-dimensional (3-D) images of scanned biological structures and/or tissue associated therewith during therapeutic procedures.

Another significant advantage of the invention is the provision of ultrasonic scanning apparatus, systems and methods that provide rapid and accurate three-dimensional (3-D) images of scanned biological structures and the focal point of the transmitted therapeutic energy (i.e. beam) during therapeutic procedures.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
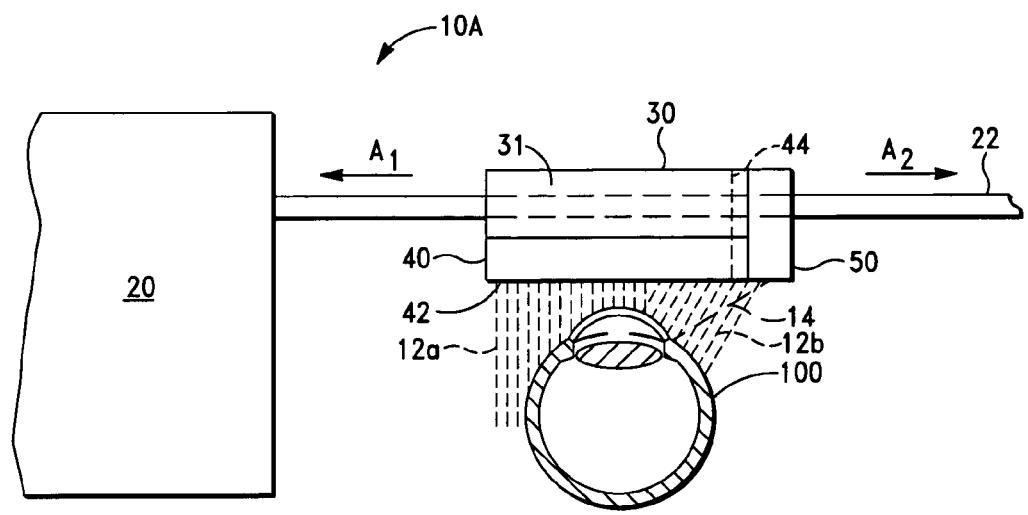
FIG. 1A is front plan view of one embodiment of a scanning apparatus positioned proximate a biological structure (i.e. an eye), in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the ultrasonic scanning apparatus, systems and methods of the invention are illustrated and described in connection with ultrasonic treatment and imaging of an eye structure, the ultrasonic scanning apparatus, systems and methods of the invention are not limited to treatment and imaging of an eye structure. According to the invention, the ultrasonic scanning apparatus, systems and methods of the invention can be readily employed to image virtually any accessible biological structure, including, without limitation, an eye structure or structure associated therewith, such as a lesion, and/or eye tissue, skin, subcutaneous tissue, mucosa and sub mucosal tissue, and the mouth, vagina, cervix, urethra and prostate, etc.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise. Thus, for example, reference to "a beam" includes two or more such beams and the like.

DEFINITIONS

The term "ultrasonic array", as used herein, means and includes a device, such as a transducer or probe, or a plurality of devices that are adapted to transmit ultrasonic energy in a spread or an array of ultrasonic beams.

The term "biological structure", as used herein, means and includes any human or animal structure or tissue associated therewith, including, without limitation, an eye structure or structure associated therewith, such as a lesion, and/or eye tissue, skin, mucosa, mouth, throat, vagina, rectum, cervix, urethra, etc.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As instated above, it is to be understood that, although the ultrasonic scanning apparatus, systems and methods of the invention are illustrated and described in connection with ultrasonic imaging and, in some instances, treatment of an eye structure or a structure associated therewith, e.g. a lesion, the ultrasonic scanning apparatus, systems and methods of the invention are not limited to imaging and treatment of an eye structure or a structure associated therewith. According to the invention, the ultrasonic scanning apparatus, systems and methods of the invention can be readily employed to image virtually any accessible biological structure and/or structure associated therewith, including, without limitation, an eye structure or structure associated therewith, such as a lesion, and/or eye tissue, skin, subcutaneous tissue, mucosa and sub mucosal tissue, and the mouth, vagina, cervix, urethra and prostate, etc.

As is well known in the art, therapeutic ultrasound can be employed to focus a transmitted ultrasonic wave for a short distance inside a target tissue for cosmetic purposes. However, this requires focusing the ultrasonic wave at an angle to be focused inside the tissue.

It is not, however, possible to observe the focused therapeutic beam with a single B-scan unit. Since the beam needs to be angulated to focus the ultrasonic waves, the echoes are diverged after being focused and are not strong enough to be seen with the same unit.

Further, the distance or focal point of a focused ultrasound beam from the probe surface has, and continues to be, difficult to measure inside the tissue. The focal point of a focused ultrasound beam is thus typically determined in a laboratory in vitro test, whereby the distance of the lesion from the surface of the tissue is determined under a microscope.

Alternatively, a separate ultrasonic probe can be subsequently employed after the initial tissue treatment with the therapeutic probe. However, this method requires guessing the position of the treated tissue ort structure, e.g., lesion, to observe the treated tissue or structure, e.g., thermal effect inside the tissue.

As will readily be appreciated by one having ordinary skill in the art, the present invention substantially reduces or eliminates the aforementioned disadvantages and drawbacks associated with conventional B-scan devices and methods associated therewith. As discussed in detail below, in a preferred embodiment, the scanning apparatus and systems of the invention employ a unique ultrasonic array to transmit ultrasonic energy to a biological structure, such as an eye and extraocular structures.

The ultrasonic array provides specific three-dimensional (3-D) information relating to the eye and precise volumetric information relating to structures associated therewith, such as a tumor, prior, during and/or after treatment. The ultrasonic array can also be combined with a therapeutic ultrasonic unit for real-time 3-D observation of a structure on a monitor during the treatment, e.g., treatment of a lesion as a single procedure. As indicated above, observation of a structure during treatment with a conventional scanning device typically requires a two step procedure.

Figure 2:
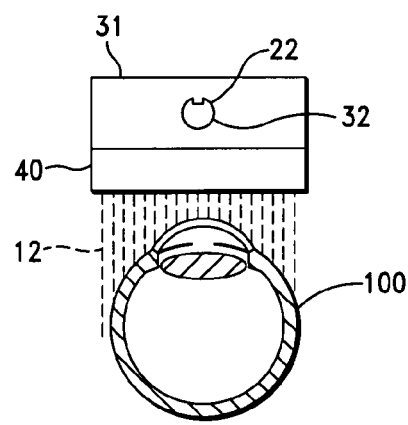
FIG. 2 is a side view of the scanning apparatus shown in FIG. 1, in accordance with one embodiment of the invention.

Referring now to FIGS. 1A and 2, there is shown one embodiment of an ultrasonic scanning apparatus 10A of the invention. As illustrated in FIG. 1A, the apparatus 10A includes a housing 20 and a linear translation rod 22. The apparatus further includes one embodiment of an ultrasonic transmission assembly 30 comprising an assembly support member 31, and an ultrasonic imaging probe 40 and therapeutic probe 50 that are connectable thereto.

According to the invention, the housing 20 is adapted to contain the apparatus control module 70, processor 72 and control system 74, discussed in detail below.

In a preferred embodiment of the invention, the apparatus rod 22 is designed and adapted to support the ultrasonic transmission assembly 30 and effectuate linear translation thereof in the directions denoted by Arrows $A_1$ and $A_2$. In the illustrated embodiment, the rod 22 has a substantially circular shape that corresponds to the assembly lumen 32 and is slidable about a portion thereof.

According to the invention, translation of the ultrasonic transmission assembly 30 on the linear translation rod 22 can be achieved by various conventional means. In one embodiment of the invention, translation of the ultrasonic transmission assembly 30 is achieved by a controlled motorized system As discussed below, linear translation of the assembly 30 is controlled by the apparatus control system (denoted "74" in FIG. 12) and is, in one embodiment, dependant on the focal point and the distance from the treatment area to the probe 40. In some embodiments, control of the linear translation of the assembly 30 is also dependant on the frequency of the ultrasound energy employed.

In some embodiments of the invention, linear translation of the assembly is preferably in the range of approximately 1-100 mm. In some embodiments, linear translation of the assembly is preferably in the range of approximately 1-30 mm.

In a preferred embodiment of the invention, the imaging probe 40 comprises an array of ultrasonic crystals that function as an emitter and receiver of ultrasonic energy, i.e. a three-dimensional (3D) ultrasonic array. In a preferred embodiment of the invention, the imaging probe (or 3D transducer) 40 includes means for redirecting or angulating the transmitted ultrasonic energy or beam(s) 12a, 12b. In FIG. 2, a side view of the ultrasonic scanning apparatus of FIG. 1 is illustrated. As depicted in this figure, the imaging probe 40 is configured to direct the ultrasonic energy or beam(s) 12 to the eye 100.

Figure 1B:
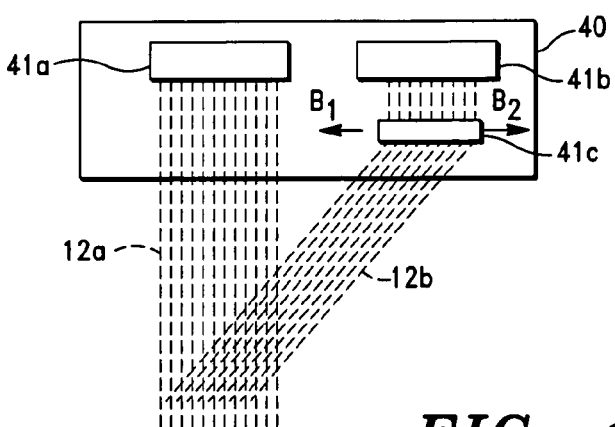
FIG. 1B is a schematic illustration of one embodiment of an imaging probe having two transducer arrays that are adapted to transmit two sets of ultrasonic beams and means for articulating one of the beam sets, according to the invention.

Referring now to FIG. 1B, in some embodiments, the imaging probe 40 includes at least two transducer arrays 41a, 41b and at least one prism 41C that is adapted to redirect or, more preferable, angulate one of the ultrasonic beams 12a or 12b (when disposed in the path thereof) to provide stereoscopic viewing of a structure. In a preferred embodiment, the imaging probe 40 also includes means for linear translation of the prism 41 in a substantially horizontal plane in the directions denoted by Arrows $B_1$ and $B_2$ to vary the degree of angulation and, hence, focus the beams 12b, i.e. beams 12a, 12b crossing or intersecting at a desired focal point.

In some embodiments of the invention, as illustrated in FIG. 1B, the prism 41C is disposed in the path of beams 12b. In some embodiments of the invention, the prism 41C is disposed in the path of beams 12a.

In some embodiments of the invention, the imaging probe 40 includes means of directly angulating one of the transducer arrays 41a or 41b and, hence, the ultrasonic beams 12a or 12b transmitted therefrom, whereby the angulated beams 12 a or 12b can similarly be focused.

Although the imaging probe 40 that is illustrated in FIG. 1A comprises an integral unit having two transducer arrays of ultrasonic crystals 41a, 41b, according to the invention, two separate imaging probes, each having a transducer array associated therewith, can be employed to generate and transmit ultrasonic beams 12a, 12b. In these embodiments, one of the probes can be adapted to angulate and, hence, angulate the transmitted beam(s) or one of the probes can include a prism (e.g., prism 41c) to angulate the transmitted beam(s).

Figure 8:
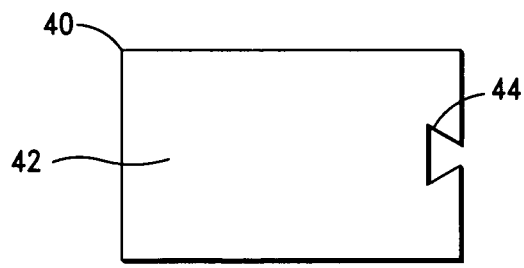
FIG. 8 is a bottom plan view of the imaging probe shown in FIG. 7, in accordance with the invention.
Figure 9:
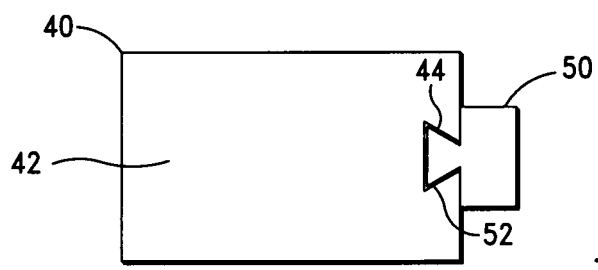
FIG. 9 is a bottom plan view of imaging probe shown in FIG. 7 connected to a therapeutic probe, in accordance with the invention.

As illustrated in FIG. 1, in certain embodiments, the energy transmitting surface 42 of the imaging probe 40 (see also FIGS. 8 and 9) preferably covers an area equal to the largest diameter of an eye 100. In some embodiments of the invention, the energy transmitting surface 42 of the imaging probe 40 thus has an area of approximately 90 mm$^2$ or more.

Figure 10:
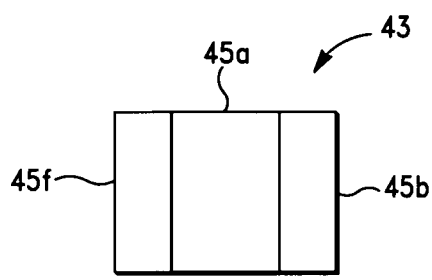
FIG. 10 is a side plan view of one embodiment of an array of imaging probes, in accordance with the invention.
Figure 11:
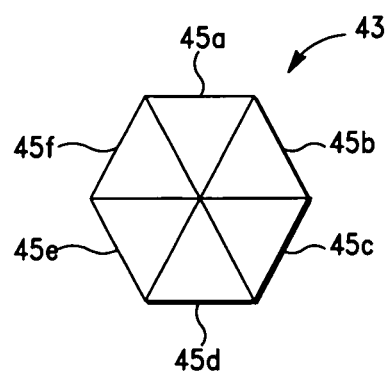
FIG. 11 is a bottom plan view of the array of imaging probes shown in FIG. 10, in accordance with the invention.

As illustrated in FIGS. 10 and 11, in an alternative embodiment of the invention, an imaging array 43, having a plurality of imaging probes 45a-45f are employed to generate and transmit the 3-D ultrasonic energy.

According to the invention, therapeutic probe 50 is preferably adapted to transmit focused therapeutic energy to target cells beneath a surface. According to the invention, various conventional therapeutic probes can thus be employed within the scope of the invention to permit three-dimensional treatment of a biological structure, such as a lesion.

In some embodiments of the invention, the therapeutic probe 50 comprises a therapeutic ultrasound probe that is adapted to transmit pulsed ultrasonic energy to target organs or cells. The pulsed waves of ultrasonic energy preferably converge in a confined focal volume, whereby a treatment of a biological structure or tissue can be achieved.

Figure 7:
FIG. 7 is a side plan view of one embodiment of an imaging probe, in accordance with the invention.

According to the invention, various means can be employed to attached the therapeutic probe 50 to the ultrasonic transmission assembly 30. In some embodiments, the assembly 30 and associated imaging probe 40 include a slot 44 that is adapted to slideably receive the projecting engagement region 52 of the therapeutic probe 50 (see FIGS. 7-9).

In some embodiments of the invention, the therapeutic probe 50 is adapted to transmit pulsed acoustic energy or waves at an angle relative to the axis of the probe 50, whereby the generated therapeutic beam 14 is focused inside the beam paths 12a, 12b of the 3-D imaging probe 40, which, as illustrated in FIG. 1, is preferably perpendicular to the tissue. This permits the focal point of the therapeutic beam 14 to be observed by the 3-D imaging probe 40.

Figure 3:
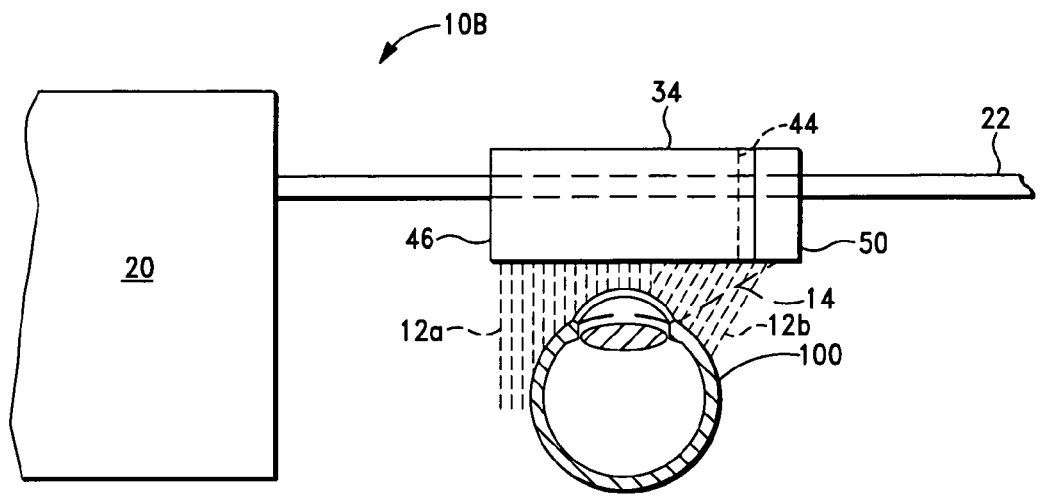
FIG. 3 is front plan view of another embodiment of a scanning apparatus positioned proximate an eye, in accordance with the invention.
Figure 4:
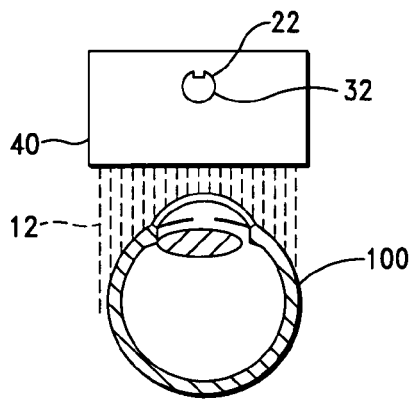
FIG. 4 is a side view of the scanning apparatus shown in FIG. 3, in accordance with one embodiment of the invention.

Referring now to FIGS. 3-4, there is shown another embodiment of an ultrasonic scanning apparatus 10B of the invention, which similarly includes the housing 20 and a linear translation rod 22. As illustrated in FIG. 3, the apparatus further includes another embodiment of an ultrasonic transmission assembly 34, which, in this embodiment, merely comprises an ultrasonic imaging probe 46, having similar functions and features as imaging probe 40, and the therapeutic probe 50. Also, like imaging probe 40, ultrasonic imaging probe 46 is configured to direct the ultrasonic energy or beam(s) 12 to the eye 100 (see FIG. 4).

As further illustrated in FIG. 3, the ultrasonic imaging probe 46 similarly includes slot 44 that is adapted to slideably receive the projecting engagement region 52 of the therapeutic probe 50.

Figure 5:
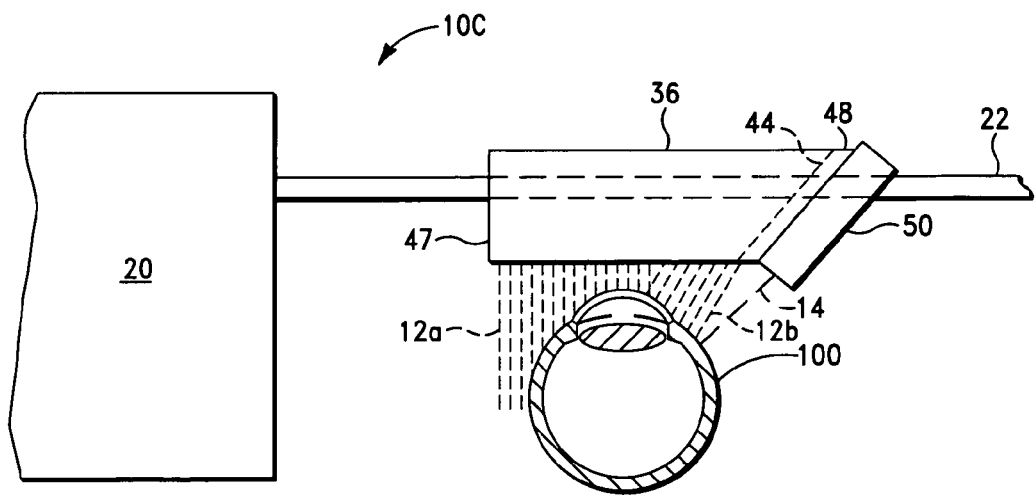
FIG. 5 is front plan view of another embodiment of a scanning apparatus positioned proximate an eye, in accordance with the invention.

Referring now to FIG. 5, there is shown another embodiment of an ultrasonic scanning apparatus 10C of the invention, which similarly includes the housing 20 and a linear translation rod 22. As illustrated in FIG. 5, the apparatus 10C further includes another embodiment of an ultrasonic transmission assembly 36 that includes ultrasonic imaging probe 47, having similar functions and features as imaging probe 40, and the therapeutic probe 50.

However, in this embodiment, the ultrasonic imaging probe 47 has an angled end 48 that is adapted to angularly mount the therapeutic probe 50 in a fixed angled orientation relative to the axis of the imaging probe 47, whereby the therapeutic beam 14 generated by the therapeutic probe 50 is focused inside the beam paths 12a, 12b of the imaging probe 47. This similarly permits the focal point of the therapeutic beam 14 to be observed by the imaging probe 40.

Figure 6:
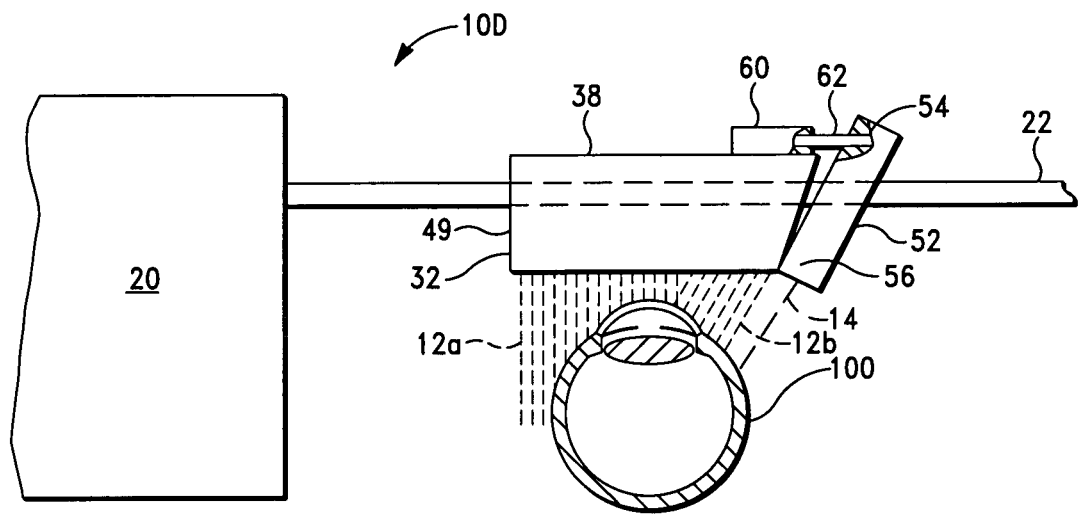
FIG. 6 is front plan view of another embodiment of a scanning apparatus positioned proximate an eye, in accordance with the invention.

Referring now to FIG. 6, there is shown another embodiment of an ultrasonic scanning apparatus 10D of the invention, which similarly includes the housing 20 and a linear translation rod 22. As illustrated in FIG. 6, the apparatus 10D further includes another embodiment of an ultrasonic transmission assembly 38 that includes ultrasonic imaging probe 49, having similar functions and features as imaging probe 40, and a therapeutic probe 52.

However, in this embodiment, the transmission assembly 38 includes control means 60 for controlling the angular orientation of the therapeutic probe 52. In some embodiments of the invention, the control means 60 includes a control shaft 62 that is operatively connected to the internal control mechanism (not shown) and probe 52. In some embodiments, the probe 52 includes a lumen 54 on one end thereof that is adapted to receive the control shaft 62.

According to the invention, various conventional means can be employed to rotatably attach the probe 52 to the imaging probe 49 proximate point 56 and extend and retract the shaft 62 to effectuate angular rotation of the probe 52 about point 56.

In some embodiments, the control means 60 includes manual adjustment means to effectuate linear translation of the control rod 62 and, hence, angular rotation of the probe 52 about point 56. In some embodiments, the control means 60 includes automated adjustment means, e.g., threaded control rod end and motor with a corresponding pinion gear, to effectuate linear translation of the control rod 62 and, hence, angular rotation of the probe 52 about point 56.

According to the invention, the apparatus 10 can generate and transmit ultrasonic energy having a frequency in the range of 1-100 MHz to target biological structures. In the case of an eye, a high (or highest) frequency of approximately 50-80 MHz would provide a depth of the entire anterior segment to slightly beyond the surface of the crystalline lens. A lower ultrasonic frequency of approx. 10-20 MHZ permits simultaneous visualization of the anterior and posterior segment.

Figure 12:
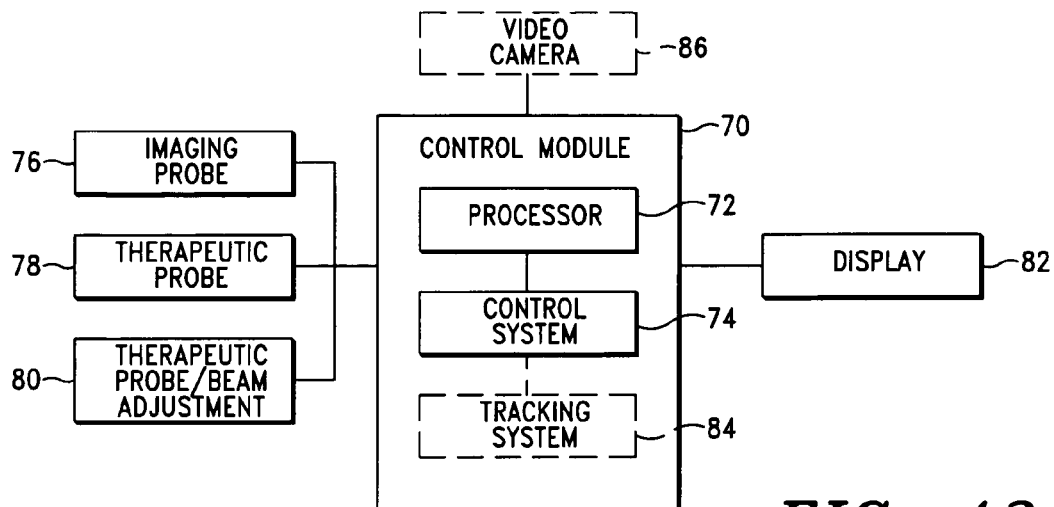
FIG. 12 is a block diagram of one embodiment of a scanning apparatus control module and associated sub-systems, in accordance with the invention.

Referring now to FIG. 12, there is shown a schematic illustration of the apparatus control module 70 and associated sub-systems or components of the apparatus, in accordance with one embodiment of the invention. As illustrated in FIG. 12, in one embodiment, the control module includes a processor 72 and control system 74.

In a preferred embodiment of the invention, the processor 72 is adapted to receive and process image signals transmitted by the imaging probe 76. The processor 72 is further adapted to generate 3-D images or representations of the scanned biological structure or tissue from the received image signals.

According to the invention, various known processing protocols can be employed to generate the 3-D images.

In some embodiments of the invention, the processor 72 is additionally programmed and adapted to filter extraneous signals to enhance the accuracy of the generated 3-D images. According to the invention, various conventional programs and techniques can be employed to filter extraneous signals.

In some embodiments of the invention, the scanning apparatus of the invention further include a video camera 86 that is positioned and adapted to record video images of the surface of the biological structure or tissue subjected to treatment.

In some embodiments, the scanning apparatus of the invention additionally include a tracking system 84 that is adapted to monitor motion of the structure subject to treatment, e.g., twitching of an eye. In some embodiments of the invention, the processor 72 is further programmed and adapted to eliminate the effect of structure motion in relationship to the probe(s).

In some embodiments, monitoring of structure motion by the tracking system 84 is facilitated by video images transmitted by the video camera 86. In these embodiments, the processor 72 program is responsive to video images transmitted by the video camera 86

According to the invention, the generated 3-D images and video images (if the video camera 86 is employed) can be transmitted to and downloaded on a separate device, such as a PC, by operatively connecting the device thereto. In some embodiments, the scanning apparatus of the invention include a visual display 82 that facilitates real-time observation of the 3-D and video images.

The control system 74, which is in communication with the processor 72, is programmed and adapted to control the imaging probe 76, including angular adjustment of the transmitted energy or beams (e.g., beams 12a, 12b), therapeutic probe 78 and angular adjustment of the therapeutic probe 80 and, hence, beam transmitted therefrom. The control system 74 is further programmed and adapted to control the linear translation of the imaging probe 76 and the associated transducer arrays, and therapeutic probe 78.

In some embodiments of the invention, the control system 74 is further adapted to control the tracking system 84 and video camera 86, if employed.

In some embodiments of the invention, control of the imaging and therapeutic probes 76, 78 comprises controlling the mode, i.e. pulsed or steady-state, frequency, initiation (i.e. start), and duration of the transmitted ultrasonic energy or beam(s). In some embodiments, control of the imaging and therapeutic probes 76, 78 also comprises synchronization of the transmitted ultrasonic energy or beam(s).

Figure 13:
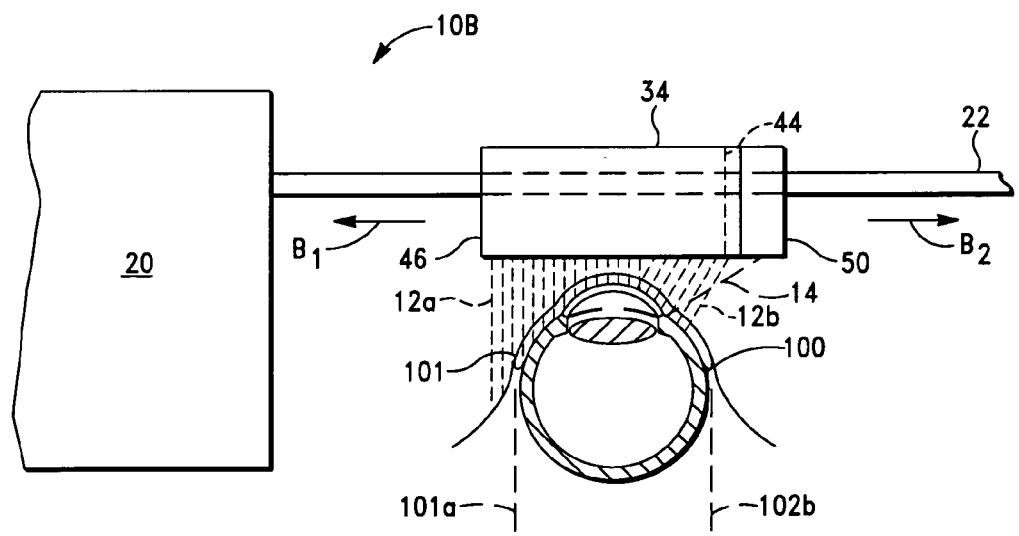
FIG. 13 is front plan view of the scanning apparatus shown in FIG. 3 during a scanning procedure on an eye, in accordance with the invention.
Figure 14:
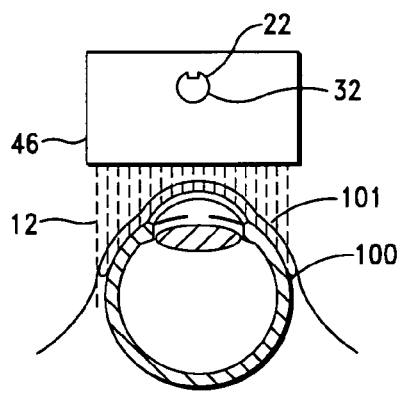
FIG. 14 is a side plan view of the scanning procedure with the imaging probe shown in FIG. 13, in accordance with one embodiment of the invention.

Referring now to FIGS. 13 and 14, an ultrasonic scanning procedure on an eye 100 with a scanning apparatus of the invention will now be described in detail. It is, however, to be understood that although the procedure (or scanning method) is described in connection with scanning apparatus 10B, the scanning method also applicable to procedures performed with other apparatus embodiments, including apparatus 10A and 10C.

As will readily be appreciated by one having ordinary skill in the art, a key advantage of the scanning apparatus and associated methodology of the invention is that direct contact with the surface of the eye 100, e.g., conjunctiva, is avoided. In a preferred embodiment of the invention, the ultrasonic energy or beam(s) is transmitted when the eye 100 is closed, i.e. through the eye lid 101.

Prior to subjecting the eye 100 to ultrasonic scanning, the scanning parameters, e.g., pulsed or steady-state, frequency, initiation (i.e. start), duration of the transmitted ultrasonic energy or beam(s), timing of linear translation of the probes 46, 50, etc., are set in the apparatus 10B.

Information relating to the structure to be treated, such as the size, location, etc. of a lesion, is also inputted into the apparatus 10B.

In some embodiments, methylcellulose gel is then initially applied on the eye lid 101, whereby the imaging probe 46 and, in some embodiments, therapeutic probe 50 are coupled to the eye lid 101.

Thereafter, the imaging and therapeutic probes 46, 50 are positioned a minimal distance from the eye lid 101 proximate the outer periphery (or edge) of the eye 100 (denoted by lines 101a, 102b). In some embodiments, the imaging probe 46 is positioned at a distance in the range of approximately 1-5 mm from the eye lid 101. In some embodiments, the imaging probe 46 is positioned at a distance of approximately 0.5 mm from the eye lid 101.

In some embodiments, the therapeutic probe 50 is positioned at a distance in the range of approximately 1-4 mm from the eye lid 101. In some embodiments, the therapeutic probe 50 is positioned at a distance of approximately 0.5 mm from the eye lid 101.

The scanning procedure is then initiated, whereby the predetermined ultrasonic energy is transmitted by the imaging and therapeutic probes 46, 50 while the probes 46, 50 are automatically moved across the eye (or a defined structure or tissue thereof) slowly on the apparatus rod 22 in a direction denoted by Arrow $B_1$ or in a direction denoted by Arrow $B_2$ (depending on which edge of the eye 101 the probes 46, 50 are initially positioned).

If a video camera 86 is employed, a visual recording of the eye or eye structure is also initiated with the camera 86.

In some embodiments, the imaging and therapeutic probes 46, 50 are linearly translated or moved a distance in the range of approximately 30-35 mm over a duration of time in the range of approximately 1-2 min while scanning the entire eye 100 from the front to the back. In some embodiments, the imaging and therapeutic probes 46, 50 are linearly translated or moved a distance in the range of approximately 35-45 mm over a duration of time in the range of approximately 10-1000 sec.

The scanning data obtained by the imaging and therapeutic probes 46, 50 (and video recording, if a video camera is employed) is then transmitted to the processor 72, processed to generate 3-D images of the treatment area, whereby the focal point of the therapeutic energy or beam 14 can be observed in 3-D format on the apparatus display 82 or on the screen of a separate device, e.g. PC or PDA, operatively connected to the apparatus 10B.

This permits not only precise localization of the treatment area, but also provides real-time information, such as degree of thermal effect, coagulation of tissue and achieved shrinkage of the treated area. This also allows an operator to adjust the location and/or power of the beam transmitted by the therapeutic probe 50.

According to the invention, the processor 72 can generate and provide the 3-D images within a period of time in the range of approximately 1-2 min., more preferably, in the range of approximately 30 sec.-1 min.

The scanning data obtained by the imaging and therapeutic probes 46, 50 and generated 3-D images (and video recording) are also stored in the processor 72, whereby selective 3-D images can be retrieved and displayed for subsequent analysis in any direction. Further, any eye structure can be seen, and the dimension and/or volume of any potential lesion(s) can be accurately determined.

A similar process can be performed with scanning apparatus 10D. However, in this instance, the angle of the therapeutic probe 52 is initially inputted into the apparatus 10D, i.e. processor 72, and set and controlled by the linear translation control means 60. The angle of the probe 52 and, hence, focal point of the therapeutic beam transmitted therefrom can also be monitored and adjusted during the scanning procedure.

It is also to be understood that this invention is not limited to particularly exemplified apparatus, systems, structures or methods as such may, of course, vary. Indeed, one of ordinary skill can make various changes and modifications to the invention to adapt it to various usages and conditions. By way of example, the therapeutic probe can be adapted to swivel relative to the imaging probe or employing a therapeutic laser with the imaging probe, whereby the focal point of the laser can be directed inside the tissue for any purpose, e.g. coagulation, photodynamic or crosslinking ablative or explosive effect. Accordingly, the present invention embraces all such alternatives, modifications and variances which are properly, equitably, and intended to be, within the full scope and range of equivalence of the following claims.

What is claimed is:

1. A scanning apparatus for biological structures, comprising:

an imaging probe that includes a first transducer, a second transducer, an energy transmitting surface, and at least one linearly displaceable prism disposed between one of said first and second transducers and said energy transmitting surface, said first transducer being configured to generate and transmit at least a first beam of ultrasonic energy to an eye structure, said second transducer being configured to generate and transmit at least a second beam of ultrasonic energy to said eye structure, said first beam of ultrasonic energy having a first energy path and a first focal point, said second beam of ultrasonic energy having a second energy path and a second focal point, said at least one linearly displaceable prism displaceable in a substantially horizontal plane intersecting a path of one of said first and second beams of ultrasonic energy, said at least one linearly displaceable prism being configured to angulate one of said first and second beams of ultrasonic energy relative to the other of said first and second beams of ultrasonic energy such that said first focal point is disposed proximate to said second focal point and stereoscopic visualization of said eye structure is provided, said imaging probe additionally configured to receive incoming ultrasonic energy from said eye structure;

a therapeutic probe that is adapted to generate and transmit pulsed therapeutic energy generally perpendicular to a surface of said eye structure, said therapeutic energy having a third energy path and a third focal point, said therapeutic probe being configured to focus said third energy path within at least one of said first and second energy paths such that said third focal point is visible to said imaging probe, said imaging probe comprising an angled end that is configured to angularly accommodate said therapeutic probe, and an outer surface from which said therapeutic energy of said therapeutic probe emanates being disposed at an obtuse angle relative to said energy transmitting surface of said imaging probe;

angular adjustment means configured to adjust an angular orientation of said therapeutic probe relative to said imaging probe, said angular adjustment means comprising a control rod that is received within a lumen disposed at one end of said therapeutic probe, whereby a linear translation of said control rod adjusts said angular orientation of said therapeutic probe;

means for simultaneous linear translation of said imaging and therapeutic probes proximate said eye structure, said means for simultaneous linear translation of said imaging and therapeutic probes comprising a linear translation rod extending in an axial direction along a length of said energy transmitting surface, said imaging and therapeutic probes being coupled to said linear translation rod, one of said first and second transducers being disposed between said at least one linearly displaceable prism and said linear translation rod;

an apparatus control system configured to control said imaging probe, said therapeutic probe, and said means for simultaneous linear translation of said imaging and therapeutic probes;

a tracking system that is configured to track motion of said eye structure subject to treatment; and a processor that is programmed and adapted to receive scanning data generated from said incoming ultrasonic energy received by said imaging probe and to generate three-dimensional images of said eye structure therefrom, said processor being further programmed and adapted to process said motion of said eye structure and to eliminate the effect of said eye structure motion relative to said imaging probe and said therapeutic probe.

2. The scanning apparatus of claim 1, wherein said energy transmitting surface of said imaging probe has an area of at least approximately 90 mm$^2$.

3. The scanning apparatus of claim 1, wherein said apparatus control system is further adapted to control at least one of said first and second beams of ultrasonic energy transmitted by said imaging probe and said therapeutic energy transmitted by said therapeutic probe.

4. The scanning apparatus of claim 3, wherein at least one of said first and second beams of ultrasonic energy transmitted by said imaging probe has a frequency in the range of approximately 1-100 MHz.

5. The scanning apparatus of claim 1, wherein said therapeutic probe comprises a therapeutic ultrasound probe.

6. The scanning apparatus of claim 1, wherein said therapeutic probe comprises a therapeutic laser probe.

7. The scanning apparatus of claim 1, wherein said processor is further adapted and programmed to filter extraneous signals to enhance the accuracy of said generated three-dimensional images.

8. The scanning apparatus of claim 1, wherein said apparatus includes a video camera, wherein monitoring of said eye structure motion by said tracking system is facilitated by video images transmitted by said video camera, and wherein said processor is further programmed and adapted to be responsive to said video images transmitted by said video camera.

9. A scanning apparatus for biological structures, comprising:

an imaging probe that includes a first transducer, a second transducer, and an energy transmitting surface, said first transducer being configured to generate and transmit at least a first beam of ultrasonic energy to an eye structure, said second transducer being configured to generate and transmit at least a second beam of ultrasonic energy to said eye structure, said first beam of ultrasonic energy having a first energy path and a first focal point, said second beam of ultrasonic energy having a second energy path and a second focal point, said imaging probe additionally configured to receive incoming ultrasonic energy from said eye structure;

means for controlling at least one of said first and second transducers, said means for controlling at least one of said first and second transducers being configured to angulate one of said first and second beams of ultrasonic energy relative to the other of said first and second beams of ultrasonic energy such that said first focal point is disposed proximate to said second focal point and stereoscopic visualization of said eye structure is provided;

a therapeutic probe that is adapted to generate and transmit pulsed therapeutic energy generally perpendicular to a surface of said eye structure, said therapeutic energy having a third energy path and a third focal point, said therapeutic probe being configured to focus said third energy path within at least one of said first and second energy paths such that said third focal point is visible to said imaging probe, said imaging probe comprising an angled end that is configured to angularly accommodate said therapeutic probe, and an outer surface from which said therapeutic energy of said therapeutic probe emanates being disposed at an obtuse angle relative to said energy transmitting surface of said imaging probe;

angular adjustment means configured to adjust an angular orientation of said therapeutic probe relative to said imaging probe, said angular adjustment means comprising a control rod that is received within a lumen disposed at one end of said therapeutic probe, whereby a linear translation of said control rod adjusts said angular orientation of said therapeutic probe;

a linear translation assembly including an elongated rod extending in an axial direction along a length of said energy transmitting surface of said imaging probe and a displaceable assembly support member having a lumen disposed therethrough for receiving said elongated rod, said imaging probe and said therapeutic probe each being attached to said displaceable assembly support member such that said imaging and therapeutic probes are capable of being simultaneously translated in a linear manner;

an apparatus control system configured to control said imaging probe, said therapeutic probe, and linear translation of said displaceable assembly support member;

a tracking system that is configured to track motion of said eye structure subject to treatment;

a processor that is programmed and adapted to receive scanning data generated from said incoming ultrasonic energy received by said imaging probe and to generate three-dimensional images of said eye structure therefrom, said processor being further programmed and adapted to process said motion of said eye structure and to eliminate the effect of said eye structure motion relative to said imaging probe and said therapeutic probe; and a housing, said elongated rod being attached to an outer surface of said housing, and said housing being configured to contain said apparatus control system and said processor.

10. The scanning apparatus of claim 9, wherein said displaceable assembly support member linearly translates in a range between approximately 1 mm and 100 mm.

11. The scanning apparatus of claim 9, wherein said energy transmitting surface of said imaging probe has an area of at least approximately 90 mm$^2$.

12. A scanning apparatus for biological structures, comprising:

an imaging probe that includes a first transducer, a second transducer, an energy transmitting surface, and at least one linearly displaceable prism disposed between one of said first and second transducers and said energy transmitting surface, said first transducer being configured to generate and transmit at least a first beam of ultrasonic energy to an eye structure, said second transducer being configured to generate and transmit at least a second beam of ultrasonic energy to said eye structure, said first beam of ultrasonic energy having a first energy path and a first focal point, said second beam of ultrasonic energy having a second energy path and a second focal point, said at least one linearly displaceable prism displaceable in a substantially horizontal plane intersecting a path of one of said first and second beams of ultrasonic energy, said at least one linearly displaceable prism being configured to angulate one of said first and second beams of ultrasonic energy relative to the other of said first and second beams of ultrasonic energy such that said first focal point is disposed proximate to said second focal point and stereoscopic visualization of said eye structure is provided, said imaging probe additionally configured to receive incoming ultrasonic energy from said eye structure;

a therapeutic probe having a longitudinal axis, said therapeutic probe being adapted to generate and transmit pulsed therapeutic energy generally perpendicular to a surface of said eye structure at an obtuse angle relative to said longitudinal axis of said therapeutic probe, said therapeutic energy having a third energy path and a third focal point, said therapeutic probe being configured to focus said third energy path within at least one of said first and second energy paths such that said third focal point is visible to said imaging probe, said imaging probe comprising an angled end that is configured to angularly accommodate said therapeutic probe, and an outer surface from which said therapeutic energy of said therapeutic probe emanates being disposed at an obtuse angle relative to said energy transmitting surface of said imaging probe;

angular adjustment means configured to adjust an angular orientation of said therapeutic probe relative to said imaging probe, said angular adjustment means comprising a control rod that is received within a lumen disposed at one end of said therapeutic probe, whereby a linear translation of said control rod adjusts said angular orientation of said therapeutic probe;

means for simultaneous linear translation of said imaging and therapeutic probes proximate said eye structure, said means for simultaneous linear translation of said imaging and therapeutic probes comprising a linear translation rod extending in an axial direction along a length of said energy transmitting surface, said imaging and therapeutic probes being coupled to said linear translation rod, one of said first and second transducers being disposed between said at least one linearly displaceable prism and said linear translation rod;

an apparatus control system configured to control said imaging probe, said therapeutic probe, and said means for simultaneous linear translation of said imaging and therapeutic probes;

a tracking system that is configured to track motion of said eye structure subject to treatment; and a processor that is programmed and adapted to receive scanning data generated from said incoming ultrasonic energy received by said imaging probe and to generate three-dimensional images of said eye structure therefrom, said processor being further programmed and adapted to process said motion of said eye structure and to eliminate the effect of said eye structure motion relative to said imaging probe and said therapeutic probe.

13. The scanning apparatus of claim 12, wherein said apparatus further includes a video camera, wherein monitoring of said eye structure motion by said tracking system is facilitated by video images transmitted by said video camera, and wherein said processor is further programmed and adapted to be responsive to said video images transmitted by said video camera.

14. The scanning apparatus of claim 13, wherein said apparatus further includes a visual display device operatively coupled to said imaging probe and said video camera, said visual display device being configured to display said three-dimensional images generated from said incoming ultrasonic energy received by said imaging probe, and said visual display device further being configured to display said video images transmitted by said video camera.

15. The scanning apparatus of claim 12, wherein said energy transmitting surface of said imaging probe has an area of at least approximately 90 mm$^2$.

\* \* \* \* \*